United States Patent [19]

Grolman et al.

[11] 4,208,800
[45] Jun. 24, 1980

[54] METHOD FOR MAKING OPHTHALMIC MEASUREMENTS

[75] Inventors: Bernard Grolman, Worcester; William Richards, Medway, both of Mass.

[73] Assignee: American Optical Corporation, Southbridge, Mass.

[21] Appl. No.: 697,906

[22] Filed: Jun. 21, 1976

Related U.S. Application Data

[62] Division of Ser. No. 679,083, Oct. 2, 1975, Pat. No. 4,055,900.

[51] Int. Cl.² ............................................. A61B 3/10
[52] U.S. Cl. ................................. 33/200; 33/174 D
[58] Field of Search ................ 33/200, 174 D; 351/5, 351/178

[56] References Cited

U.S. PATENT DOCUMENTS

2,491,312  12/1949  Henry et al. ........................... 33/200

*Primary Examiner*—Willis Little
*Attorney, Agent, or Firm*—Jeremiah J. Duggan; Alan H. Spencer; Stephen A. Schneeberger

[57] ABSTRACT

A device for use in the art of fitting lenses to spectacle frames wherewith ophthalmic measurements are applied directly to frames selected by patients. A frame without lenses is adjusted to fit the patient, the measuring device is then applied to the frame and the whole placed upon the face. Horizontal and vertical measurements of distances from lateral and inferior points on the frame rims to a desired location of lens optical center relative to pupil are made for each eye and these measurements are forwarded to the lens finishing shop for edging and fitting of the lenses.

2 Claims, 8 Drawing Figures

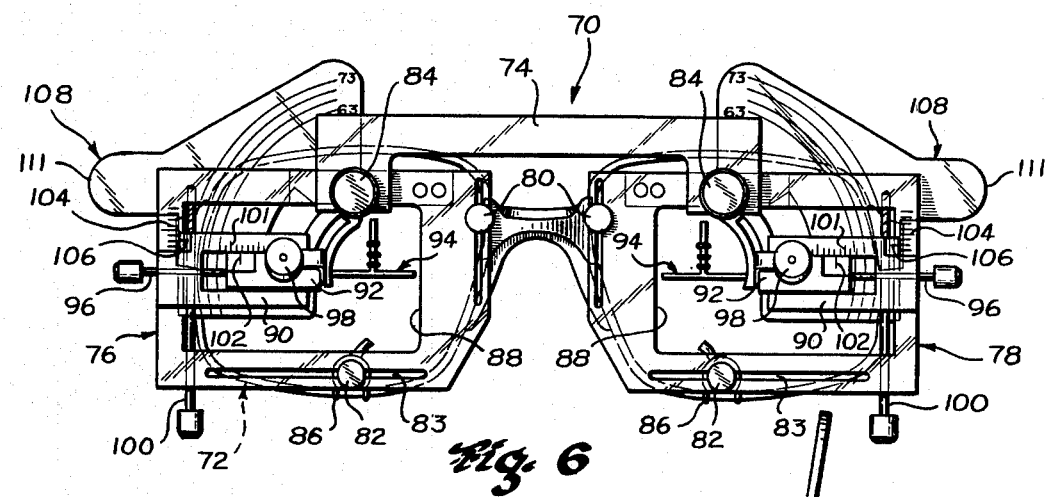
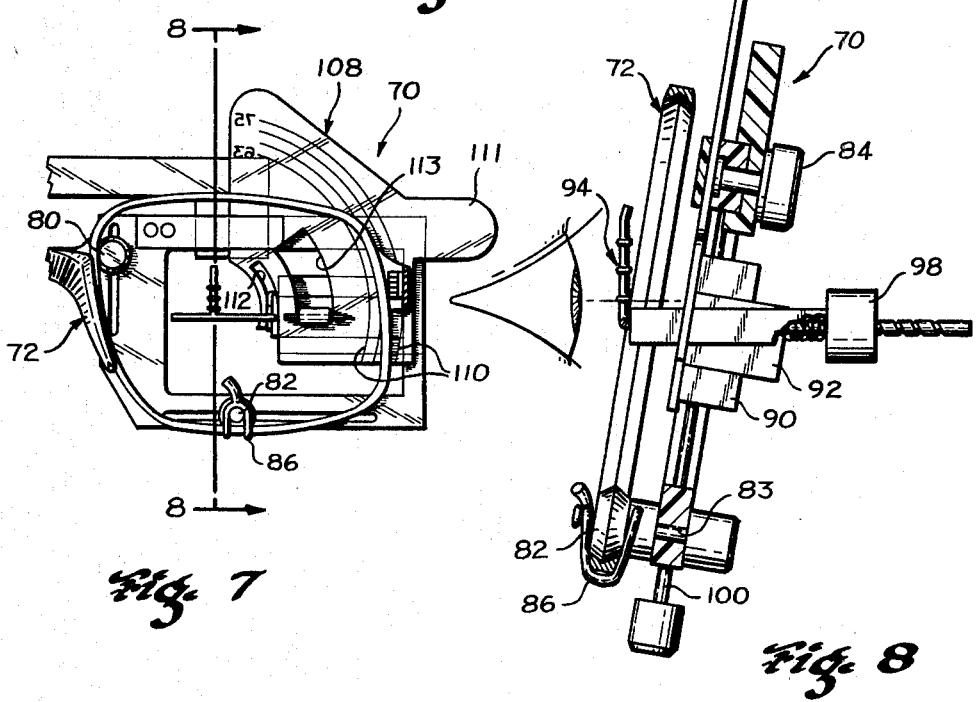

METHOD FOR MAKING OPHTHALMIC MEASUREMENTS

This is a division, of application Ser. No. 619,083 now U.S. Pat. No. 4,055,900 filed Oct. 2, 1975.

BACKGROUND OF THE INVENTION

1. Field of the Invention

This invention relates to improvements in measuring apparatus and method for use in fitting ophthalmic lenses in spectacle frames and has particular reference to applying the ophthalmic measurements directly to frames selected by the patient.

2. Description of the Prior Art

The fitting of lenses to various types of frames selected by patients is ordinarily a tedious, time-consuming and relatively difficult undertaking requiring special skills. It having been generally recognized that the several measurements necessary for optimum ophthalmic glazing are critical, various aids including special scales Pupilometers and frame or lens measuring fixtures have been recommended for obtaining some measurements.

While these lens fitting aids may relieve some of the problems and tediousness in measuring for lens fitting, the accuracy of fitting continues to rely heavily upon the skill and painstakingness of the practitioner together with similar carefulness in proper interpretation and use of the measuring information in the lens finishing shop.

Prior art approaches to applying measurements directly to patient's frames as described in expired U.S. Pat. No. 2,491,312, for example, have required ungainly and overly complicated apparatuses supplying only the heretofore conventional measurements of pupillary distance (PD) from the center of the frame and vertical height of bifocal segment, for example, in each case. These prior art apparatuses additionally require the learning and practice of relatively complicated operating procedures which are individual to each and require a multiplicity of properly sequentially performed steps, e.g. of measuring one lens fitting parameter, neutralizing instrument components and individually measuring another parameter.

Instrument costliness, ungainliness and tediousness of operation have, for the most part, outweighed and discouraged the adoption of these prior art devices in fitting practices in spite of obvious advantages of their applying measurements to the frames.

It is a principal object of the present invention to eliminate conventional measurements, including monocular pupillary distances, yet provide data necessary and sufficient for optimal glazing of ophthalmic frames. The invention applies measurements directly to preselected frames in properly fitted actual positions of use and the measurements taken are directly applicable to the established practice of boxing layout in preparing of ophthalmic lens glazing. Those interested in details of the boxing method may refer to "The Boxing Method of Specifying Eye Size" by by Glen A. Frye, PhD, *Journal of the American Optometric Association*, February 1959 pages 481-484.

SUMMARY OF THE INVENTION

The foregoing objective and its corollaries are accomplished by provision of an ophthalmic measuring device which may be mounted upon an unglazed but properly fitted spectacle frame. The device includes a vertically and horizontally adjustable reticle positionable before each eye of a patient once he is fitted with his intended spectacle frames and the measuring device is attached.

Each reticle is adjustable toward and away from a respective eye through a corresponding one of the unglazed lens rims and may be brought into juxtaposition with the eye for avoiding errors of parallax in aligning a preselected point on the reticle with a preselected part of the eye (e.g. the center of the pupil).

With the eye properly fixated for forward vision, this alignment, horizontally and/or vertically, of the reticle in each case establishes the optimum location of optical center of a lens to be mounted relative to the extreme lateral and the extreme inferior edges of a respective lens rim. The instrument is provided with scales and/or indicia indicating measurements of distances corresponding to amounts of horizontal and vertical displacement of the preselected point on the reticle from edges of the lens rims. These measurements are directly applicable to the standard ophthalmic lens boxing method of layout for glazing and are supplied to the optical shop for lens finishing and glazing.

Details of the invention will become more readily apparent from the following description when taken in conjunction with the accompanying drawings in which:

FIG. 6 is a front elevational view of another modification of the invention;

FIG. 7 is a fragmentary rear view of the apparatus of FIG. 6;

FIG. 8 is an enlarged cross-sectional view taken generally along line 8—8 of FIG. 7.

DESCRIPTION OF THE PREFERRED EMBODIMENTS

Figure 1:
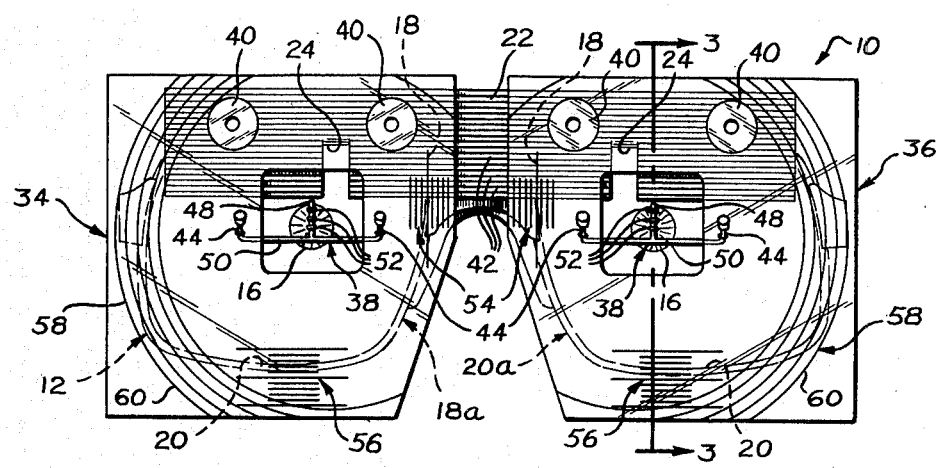
FIG. 1 is a front elevational view of one embodiment of measuring apparatus shown in a position of use upon a spectacle frame.
Figure 2:
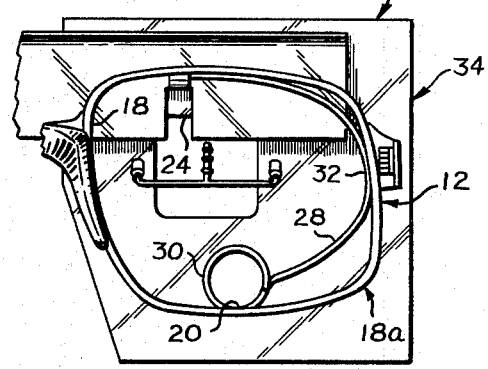
FIG. 2 is a fragmentary rear view of the combined spectacle frame and measuring apparatus of FIG. 1.
Figure 3:
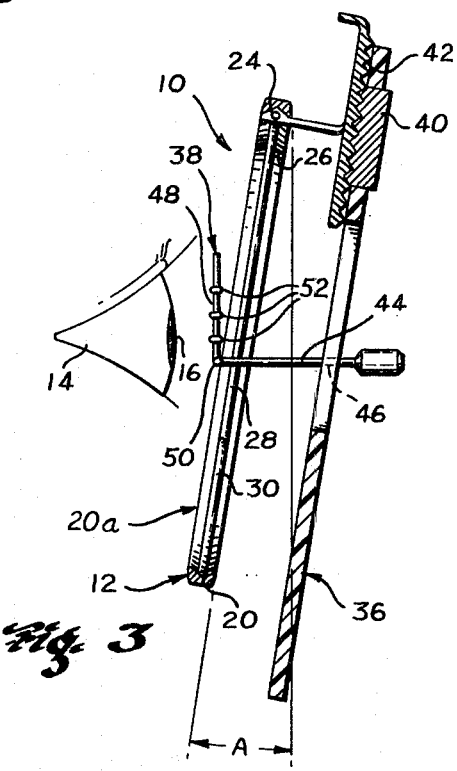
FIG. 3 is an enlarged cross-sectional view taken generally along line 3—3 of FIG. 1.

FIGS. 1-3 illustrate one embodiment of the invention (measuring device 10) mounted in a position of use upon an empty (unglazed) spectacle frame 12 which is properly adjusted and fitted upon a patient.

For ease and clarity of illustration, the eye 14 (FIG. 3) is the only part of the patient which is shown. Similarly, in FIG. 1 only the pupil 16 of each eye 14 is illustrated with a circle.

It will become apparent as this description progresses that the principal points of reference used in taking measurements with device 10 for right and left lens glazing according to the invention are: pupil 16 of the patient's eyes or portions therearound and the extreme lateral and extreme inferior edges 18 and 20 respectively of each right and left spectacle lens rim 18a and 20a.

Measuring device 10 comprises a main supporting brow bar preferably constructed of sheet steel. A pair of clips 24 (FIGS. 2 and 3) are formed upon bar 22 for use in attaching device 10 to spectacle frame 12. Clips 24 are configured to fit within grooves 26 of rims 18a and 20a as best shown in FIG. 3 and spring wires 28 extending from each of clips 24 complete the attachment. The wires 28 are provided with finger loops 30 which facilitate their placement into lowermost portions of the lens grooves (FIGS. 2 and 3). This prevents up or down displacement of brow bar 22. Bends 32 (FIG. 2) in wires 28, by resting against lateral portions of rims 18a and 20a, prevent lateral displacement of brow bar 22.

Measuring plates 34 and 36, each carrying an inverted T-shaped reticle 38, are formed of a transparent sheet plastic material and supported upon brow bar 22 by permanent magnets 40. Magnets 40 extend through plates 34 and 36 and are press-fitted, cemented, or otherwise fixed thereinplace.

Brow bar 22 is provided with horizontal serrations 42 and matching serrations are provided on the receiving faces of magnets 40 so that, without interference with horizontal sliding adjustment of plates 34 and 36, the plates are prevented from accidentally tilting relative to the brow bar. They are, nevertheless, slideably adjustable up and down on bar 22 by applying a slight lifting of the magnets over serrations on the bar.

Reticle 38 in each of plates 34 and 36 is formed of wire having legs 44 slideably extended through openings 46. As can been seen in FIG. 3, openings 46 are directed obliquely through the plates at an angle such that right angularly related legs 44 and upright extension 48 of the inverted T configuration are disposed horizontally and vertically respectively when the pantoscopic tilt, angle A of frame 12, produces the normal wearing downward and inward inclination of the frame front in its use position, i.e. as diagrammatically illustrated in FIG. 3.

In operation of measuring device 10 with spectacle frame 12 properly fitted and mounted upon the patient's face, plates 34 and 36 are brought to positions where their respective reticles are approximately horizontally and vertically aligned with the patient's eyes 14. The reticles are then each moved to positions close to corneas of the eyes by sliding legs 44 in openings 46. A position where eyelashes just clear upright 48 is appropriate for eliminating most, if not all, errors of parallax during subsequent sighting by the practitioner in operation of the measuring device 10.

Considering the horizontal wire 50 of reticle 38 as representing a position corresponding to the lower limit of a distance portion of a multifocal lens to be used in frame 12, for example, and the index marks 52 on upright 48 as being in increments of two millimeter spacings from wire 50, a particular index mark 52, or the intersection between upright 48 and wire 50, may be selected as a reference point at which the optical center of the finished lens is to be located in frame 12. If, for example, the first index mark 52 above wire 50 is selected, it will become apparent that the results of using measuring device 10 will locate the optical center of the lens two millimeters above the lower limits of the distance portion of the multifocal lens or, in other words, two millimeters above the upper limits of the reading portion of a bifocal lens.

It should be understood that device 10 may be used in conjunction with any and all forms of multifocal lenses and even single vision lenses for locating reading segment tops and/or lens optical centers in proper position for optimum glazing.

With the patient given a fixation point at approximately arms length, e.g. with the patient's eyes fixated on the practitioner's right eye for measurement of the patient's left eye, plate 36 is moved over brow bar 22 as is required to locate a selected index mark (e.g. the first mark 52 above wire 50 of reticle 38) relative to pupil 16.

The selected index mark, which can include the point of intersection of wire 50 and upright 48, may be located at the center of the pupil 16, the lower pupil edge, the inferior iris margin or elsewhere at the discretion of the practitioner usually depending upon the nature of the patient's visual acuity and posture.

Having so aligned reticle 38 with a patient's eye (e.g. the left eye in FIG. 1), scales 54 and 56 are read relative to the extreme lateral edge 18 and the extreme inferior edge 20 of lens rims 20. This reading of scales 54 and 56 relative to rim 20a is made possible by the transparency of material of the plate 36. It should be understood that the scales 54 and 56 as well as others to be described hereinafter may be calibrated to indicate distances from innermost edges of the spectacle frame rims or distances including the depth of lens rim grooves such as groove 26, for example. Accordingly, all reference hereinafter to measurement being taken to extreme lateral and/or inferior extensions of lens rims are intended to include distances to either the innermost edges of the rims or to the full depth of lens groove, whichever may be most suitable for particular requirements.

Scales 54 and 56 as well as others to be described hereinafter may be in increments of millimeters or fractions of an inch, whichever is deemed most appropriate or desirable.

Next observed is an additional arcuate scale 58, each line of which represents the position which the edge of a lens blank of designated size would assume with the optical center of a lens aligned in frame 12 as just described. Accordingly, a lens blank of outer diametral size equal to or greater than that represented by line 60 would be required to fill the complete area encompassed by rim 20a (not the lower right corner of rim 20a as viewed in FIG. 1).

Figure 5:
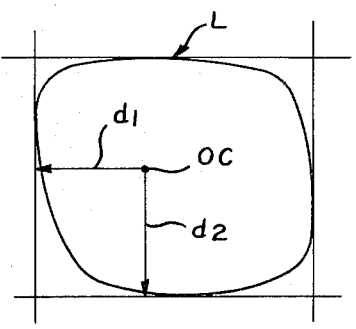
FIG. 5 illustrates the applicability of ophthalmic measurements obtained according to the invention.

Measurements obtained as above, being directly applicable to the standard boxing method of lens layout and edge finishing for glazing, are supplied to the optical shop. As shown in FIG. 5, a finished lens L would have its optical center (OC) located inwardly from the extreme nasal edge a distance $d_1$, vertical dimension $d_2$, frame eyewear (lens rim) and bridge size and diameter of lens blank (blank size) required.

While the foregoing description has been directed primarily to matters of glazing the left rim 20a of spectacle frame 12 (FIG. 1), it should be apparent that measuring for glazing of the right rim 18a would be similarly accomplished.

Figure 4:
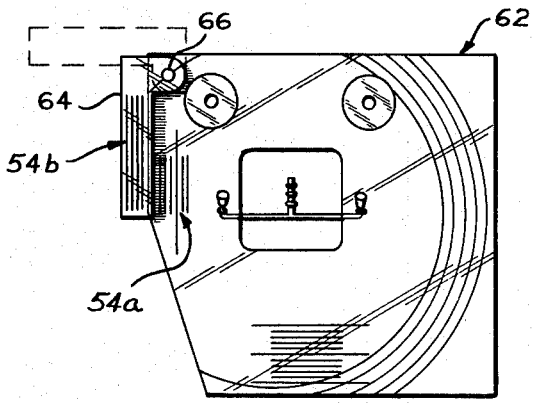
FIG. 4 is a front elevational view of a modification of the invention.

In FIG. 4, there is illustrated a modification of the invention wherein, for the fitting of patients with exceptionally wide pupillary distances, a plate 62 may be substituted for plate 36. Plate 62, having lateral measuring scale 54a similar to scale 54 of plate 36, is provided with an extension scale 54b. Indicia of scale 54b are applied to a transparent arm 64 pivoted at point 66 to the main body of slide 62. When needed for use, extension scale 54b may be pivoted into the position shown by full line illustration in FIG. 4. When not needed, it is preferably pivoted to an out-of-the-way position which has been illustrated with broken lines.

Plate 62 is otherwise preferably similar, if not identical, in construction to plate 36 already described. A right eye counterpart of plate 62 would replace plate 34.

Another embodiment of the invention is illustrated in FIGS. 6–8 and comprises measuring device 70 which is illustrated in a position of use upon spectacle frame 72.

Measuring device 70 includes main supporting brow bar 74 and depending right eye and left eye measuring plates 76 and 78 respectively each having a laterally disposed lens rim locator 80 and an inferior lens rim locator 82 for fixing device 70 in place upon spectacle frame 12.

Plates 76 and 78, being adjustable along brow bar 74 and adaptable to fixed clamping thereto by locks 84, are moved one relative to the other to positions where locators 80 are entered into respective right and left lens rim grooves and become disposed at the extreme lateral points of these grooves, i.e. at nasal sides thereof.

This having been done, inferior lens rim locators 82 are moved along slots 83 to extreme inferior points in the lens rim grooves and clamped to the lens rims. Elastic wraps 86 or other suitable means may be used for such clamping.

Plates 76 and 78 are provided with openings 88 within each of which is disposed a main slide 90 carrying a secondary slide 92. The latter, in turn, carries reticle 94. Reticle 94 is identical in structure and use to reticle 38 of FIGS. 1-3 and, accordingly, will not be further described.

Secondary slide 92 is movable laterally by means of adjusting screw 96 and reticle 94 may be adjusted toward and away from a patient's eye by means of adjusting knob 98.

The unit of reticle 94, slide 92 and slide 90 is adjustable up and down in its supporting plague by means of adjusting screw 100.

With a reticle 94 located relative to the pupil of a patient's eye as desired by the practitioner in the case of each of the right and left eyes, scales 101 are used to read the distance from the extreme lateral point of locator 80 to the reticle in each case. These reading are taken at index mark 102. Scales 104 are used to read the distance from the extreme inferior point of each locator 82 to a preselected point on a corresponding reticle. These readings are taken at index mark 106.

A transparent "size of lens blank" determining guide 108 is attached to the rear of each slide 92 and carries arcuate markings indicating the sizes of lens blanks required for satisfying the conditions of each alignment of reticle 94 with the patient's eye, i.e. a lens blank of a maximum diametral dimension represented by a particular arcuate marking 110 which cuts across the area circumscribed by a lens rim of spectacle frame 72 will not be satisfactory. A lens blank of a diameter corresponding to one of the arcuate markings 110 outside the area to be glazed must be used in the optical finishing shop and this data would be supplied to the shop.

For ease in making the determination of "size of lens blank," guide 108 is preferably thin and flexible whereby pushing inwardly against its tab 111 will bring markings 110 directly against the spectacle lens rims. Errors of parallax are thus obviated. Also, slots 112 and 113 permit (FIG. 7) movement of guides 108 upwardly and downwardly relative corresponding lens rims about the center of curvature of markings 110 for ease in testing both upper and lower portions of the rim for lens blank fit.

From the foregoing, it can be seen that devices of the invention eliminate the heretofore need for pupillary distance (PD) measurements and others conventionally used in establishing parameters for ophthalmic lens glazing. The present invention applies simple measurements directly to preselected spectacle frames in properly fitted actual positions of use. Furthermore, the measurements provided according to the invention are directly applicable to the long established standard practice of lens layout for edging and glazing by the boxing method.

Those skilled in the art will readily appreciate that various additional modifications and adaptations of the precise forms here shown may be made to suit particular requirements. It is, accordingly intended that such modifications which incorporate the novel concept disclosed are to be construed as coming within the scope of the claims or the range of equivalency to which they are entitled in view of the prior art.

We claim:

1. The method of making ophthalmic measurements for glazing spectacles frames comprising the steps of:
    adjusting a preselected spectacles fra,e having a pair of lens rims for proper fitting thereof to a patient's face before his two eyes;
    detachably connecting a measuring means carrying an aligning reticle to said frame with said reticle disposed within an area circumscribed by one lens rim of the frame;
    placing said frame in proper wearing position upon said patient's face with said measuring means thereconnected and said one lens rim located forwardly of one of said patient's two eyes;
    aligning in a single operation a single preselected point on said reticle with a preselected point on said one of said patient's eyes; and
    in a single step measuring from said single preselected point on said aligned reticle the distances directly therefrom to both an extreme lateral and the extreme inferior points on said lens rim of said frames, said measurements being applicable to the finishing of an opthalmic lens for glazing in said rim.

2. The method according to claim 1 wherein said measuring means includes a second aligning reticle disposed within an area circumscribed by the second lens rim of said frame and said steps of aligning and measuring are repeated in conjunction with the patient's second eye.

* * * * *